United States Patent
Vendrely et al.

(10) Patent No.: US 7,976,547 B2
(45) Date of Patent: Jul. 12, 2011

(54) CEMENT RESTRICTOR WITH INTEGRATED PRESSURE TRANSDUCER AND METHOD OF MEASURING THE PRESSURE AT THE DISTAL END OF A BONE CANAL

(75) Inventors: Timothy Vendrely, Fort Wayne, IN (US); Andrew I. Spitzer, Beverly Hills, CA (US)

(73) Assignee: DePuy Products, Inc., Warsaw, IN (US)

( * ) Notice: Subject to any disclaimer, the term of this patent is extended or adjusted under 35 U.S.C. 154(b) by 1179 days.

(21) Appl. No.: 11/018,122

(22) Filed: Dec. 21, 2004

(65) Prior Publication Data

US 2006/0149282 A1    Jul. 6, 2006

(51) Int. Cl.
A61B 17/58      (2006.01)
A61B 17/60      (2006.01)
A61F 2/00        (2006.01)

(52) U.S. Cl. .......................... 606/95; 606/94
(58) Field of Classification Search ............. 606/92–95, 606/102, 62–68; 623/22.11–23.38
See application file for complete search history.

(56) References Cited

U.S. PATENT DOCUMENTS

| | | | |
|---|---|---|---|
| 4,994,085 A | | 2/1991 | Sawai et al. |
| 5,376,120 A | * | 12/1994 | Sarver et al. ............ 623/23.58 |
| 5,591,171 A | * | 1/1997 | Brown ....................... 606/94 |
| 5,849,014 A | | 12/1998 | Mastrorio et al. |
| 5,879,403 A | | 3/1999 | Ostiguy et al. |
| 5,997,580 A | | 12/1999 | Mastrorio et al. |
| 6,280,477 B1 | | 8/2001 | Mastrorio et al. |
| 6,325,830 B1 | | 12/2001 | Mastrorio et al. |
| 6,447,448 B1 | | 9/2002 | Ishikawa et al. |
| 6,533,733 B1 | | 3/2003 | Ericson et al. |
| 6,636,769 B2 | | 10/2003 | Govari et al. |
| 6,638,231 B2 | | 10/2003 | Govari et al. |
| 6,652,464 B2 | | 11/2003 | Schwartz et al. |
| 6,658,300 B2 | | 12/2003 | Govari et al. |
| 7,295,877 B2 | * | 11/2007 | Govari ............................ 607/60 |
| 2002/0107445 A1 | | 8/2002 | Govari |
| 2003/0018246 A1 | | 1/2003 | Govari et al. |
| 2003/0120150 A1 | | 6/2003 | Govari |
| 2003/0139690 A1 | * | 7/2003 | Aebli et al. .................. 600/587 |

FOREIGN PATENT DOCUMENTS

| | | |
|---|---|---|
| JP | 01-230353 | 9/1989 |
| JP | 2003-518973 | 6/2003 |
| WO | 0149173 | 7/2001 |

OTHER PUBLICATIONS

European Search Report for European Application No. EP05257828.3-2305, Apr. 5, 2006, 7 pgs.
Japanese Office Action for Japanese Patent Application No. 2005-366828, Feb. 9, 2010, 2 pgs.

* cited by examiner

*Primary Examiner* — Eduardo C Robert
*Assistant Examiner* — Andrew Yang
(74) *Attorney, Agent, or Firm* — Barnes & Thornburg LLP

(57) ABSTRACT

A cement restrictor for use in surgical procedures such as total hip replacement, for example, includes a pressure transducer and a transmitter electrically coupled to the pressure transducer. The cement restrictor is configured to be placed at a distal end of a pre-drilled bone canal in a patient's femur, for example, such that the pressure transducer may generate an output signal in response to the presence of bone cement injected into the bone canal and around the cement restrictor. The transmitter is configured to transmit this output pressure signal to an external receiver outside the patient's body.

19 Claims, 2 Drawing Sheets

CEMENT RESTRICTOR WITH INTEGRATED PRESSURE TRANSDUCER AND METHOD OF MEASURING THE PRESSURE AT THE DISTAL END OF A BONE CANAL

FIELD OF THE DISCLOSURE

The present disclosure relates to cement restrictors for use in surgical procedures, such as total hip replacement, for example, and to instruments for measuring the pressure of bone cement injected into a canal drilled into a patient's bone, such as the femur to secure an implant within the bone.

BACKGROUND

Arthroplasty procedures, such as a total hip replacement (THR), can require the removal of the femoral head and neck, followed by implantation of an artificial hip stem into a reamed portion of the femoral medullary canal. Some hip arthroplasty procedures call for the use of bone cement to secure the hip stem within the medullary canal. For procedures that call for cement, it is generally undesirable to allow the cements to infiltrate the medullary canal to an uncontrolled depth and volume. As such, a hip arthroplasty procedure may include the step of placing an obstruction within the medullary canal in an attempt to restrict or block the flow of cement.

Cement restrictors, therefore, are often used to create a blockage within the medullary canal to block the flow of the cement into the medullary canal. Various cement restrictors are known in the art. For example, U.S. Pat. Nos. 6,280,477; 6,325,830; 5,997,580; 5,879,403; and 5,849,014 disclose various cement restrictors, the disclosures of which are incorporated by reference herein. Other commercially available cement restrictors include the BIOSTOP G® made and sold by DePuy Orthopaedics, Inc. (Warsaw, Ind.).

As mentioned above, many arthroplasty procedures such as THR, call for the use of bone cement to secure the hip stem within the medullary canal. This bone cement is oftentimes pressurized bone cement. For example, adequate cement pressurization may allow the bone cement to interdigitate into the cancellous bone. This interdigitation may aide in the long-term survival of a cemented hip stem. The bone cement may be pressurized by occluding the femoral canal at the distal end, with a cement restrictor, for example, and at the proximal end with a bone cement pressurizer used in conjunction with a bone cement injection gun.

Various proximal pressure measurement devices may be used which directly measure the pressure of the bone cement in the proximal portion of the bone canal. Such devices are often hard-wired to a visual display device to display the pressure of the bone cement for the surgeon. Other measurement systems, such as empirical measurement systems for measuring the pressure of the bone cement, use capillary type devices to determine the pressurization of the bone cement by how far the bone cement is extruded into the capillary tubes during cement pressurization. Further, known distal cement pressure measurement devices require the surgeon to perforate the cortex of the femur to allow a pressure transducer or capillary type system to sense the pressure of the bone cement at the distal end of the canal.

SUMMARY

The present invention comprises one or more of the features recited in the appended claims or the following features or combinations thereof:

A cement restrictor includes a pressure transducer and a transmitter electrically coupled to the pressure transducer and configured to transmit an output signal of the pressure transducer to a remote receiver. The cement restrictor may be placed at a distal end of a canal drilled in a patient's femur to prevent the bone cement injected into the canal from flowing into the undrilled portion of the medullary canal of the femur. The pressure transducer may read the pressure of the surrounding bone cement and generate an output pressure signal indicative of that pressure. The transmitter may then transmit this pressure signal to the remote receiver to provide the surgeon with information regarding the pressure of the bone cement at the distal end of the canal.

The cement restrictor may further include a power source electrically coupled to the pressure transducer and the transmitter. The power source may be a battery or a ferrite coil configured to produce an electric current when subjected to a magnetic field. The power source may also be a radio frequency transducer configured to produce an electric current in response to radio waves.

A body of the cement restrictor may include a channel in communication with the surrounding environment. The pressure transducer may be positioned within the channel such that the pressure transducer is also in communication with the surrounding environment. The body may further include a threaded bore in communication with the channel and configured to receive a mating portion of a cement restrictor inserter. The body of the cement restrictor may be implantable, biocompatible and/or resorbable. The body may also include high density polyethylene.

The transmitter of the cement restrictor may include a modulator configured to modulate the output pressure signal of the pressure transducer into a radio wave and an antenna configured to transmit the modulated output pressure signal to the remote receiver.

A method of measuring the pressure within a distal end of a bone canal during cement pressurization of the canal may include inserting a pressure transducer into the distal end of the bone canal, inserting pressurized bone cement into the bone canal, reading an output signal from the pressure transducer, and adjusting the pressure of the pressurized bone cement being injected into the bone canal in response to the transmitted output pressure signal of the pressure transducer. Reading the output signal may further include transmitting the output pressure signal of the pressure transducer to a remote receiver.

Alternatively, a method of injecting pressurized cement into a pre-drilled bone canal includes injecting pressurized cement at a first pressure into the pre-drilled bone canal, monitoring the pressure of the pressurized cement at a distal end of the bone canal via a wireless communication originating from the distal end of the bone canal, adjusting the pressure of the pressurized cement from the first pressure to a second pressure, and injecting pressurized cement at the second pressure into the pre-drilled bone canal.

Monitoring the pressure of the pressurized cement at the distal end of the canal may include reading the pressure at the distal end of the canal using an implanted pressure transducer and transmitting an output signal of the pressure transducer to a remote receiver. Further, transmitting the output signal of the pressure transducer to a remote receiver may include modulating the output signal to a radio-frequency wavelength.

The above and other features of the present disclosure will become apparent from the following description and the attached drawings

BRIEF DESCRIPTION OF THE DRAWINGS

The detailed description particularly refers to the accompanying figures in which.

DETAILED DESCRIPTION OF THE DRAWINGS

Figure 1:
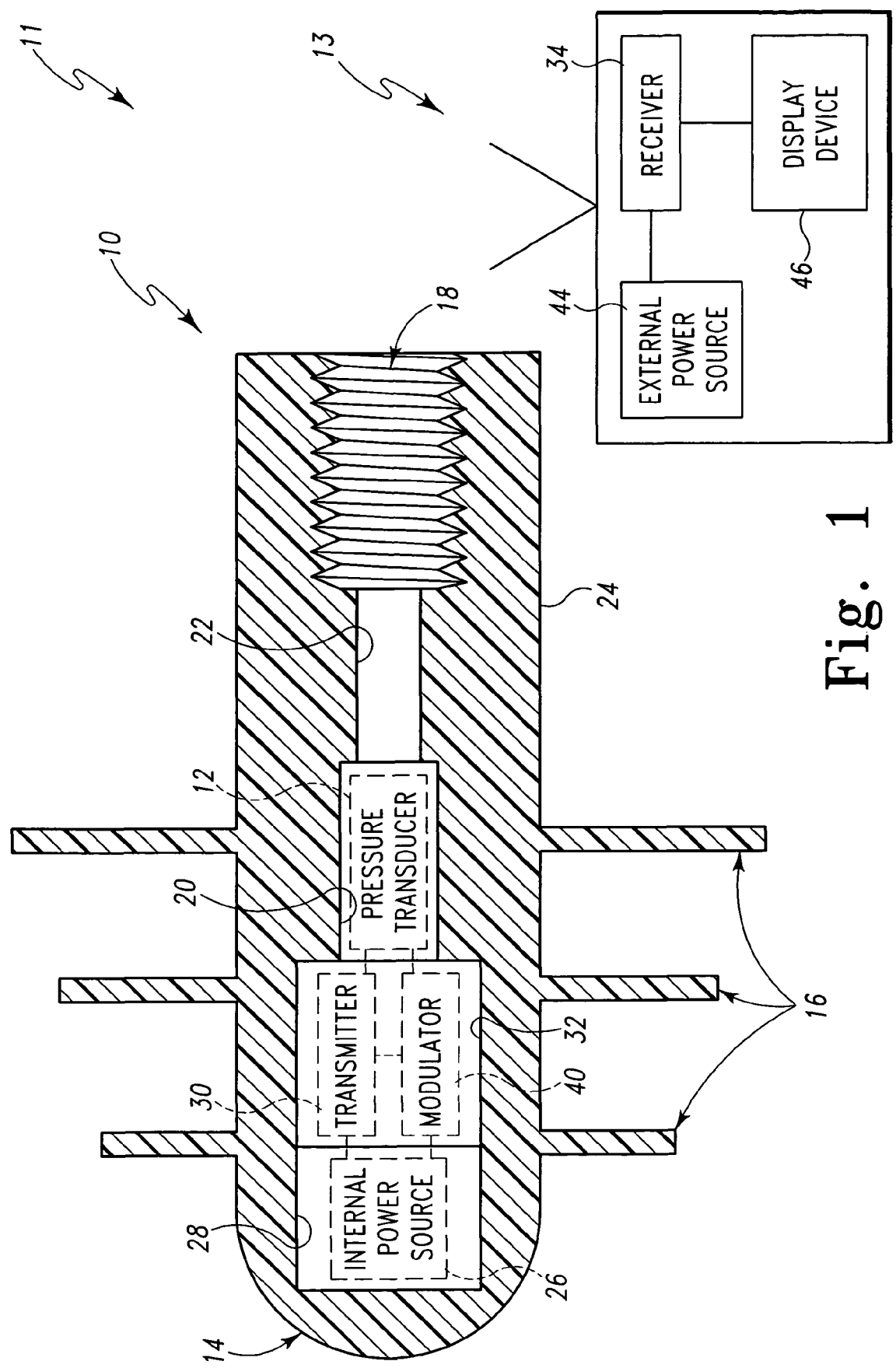
FIG. 1 is a partially schematic view of a distal cement pressure measurement system including a cement restrictor of the present disclosure having a pressure transducer and transmitter and external components including a receiver to receive and display information transmitted from the cement restrictor.
Figure 2:
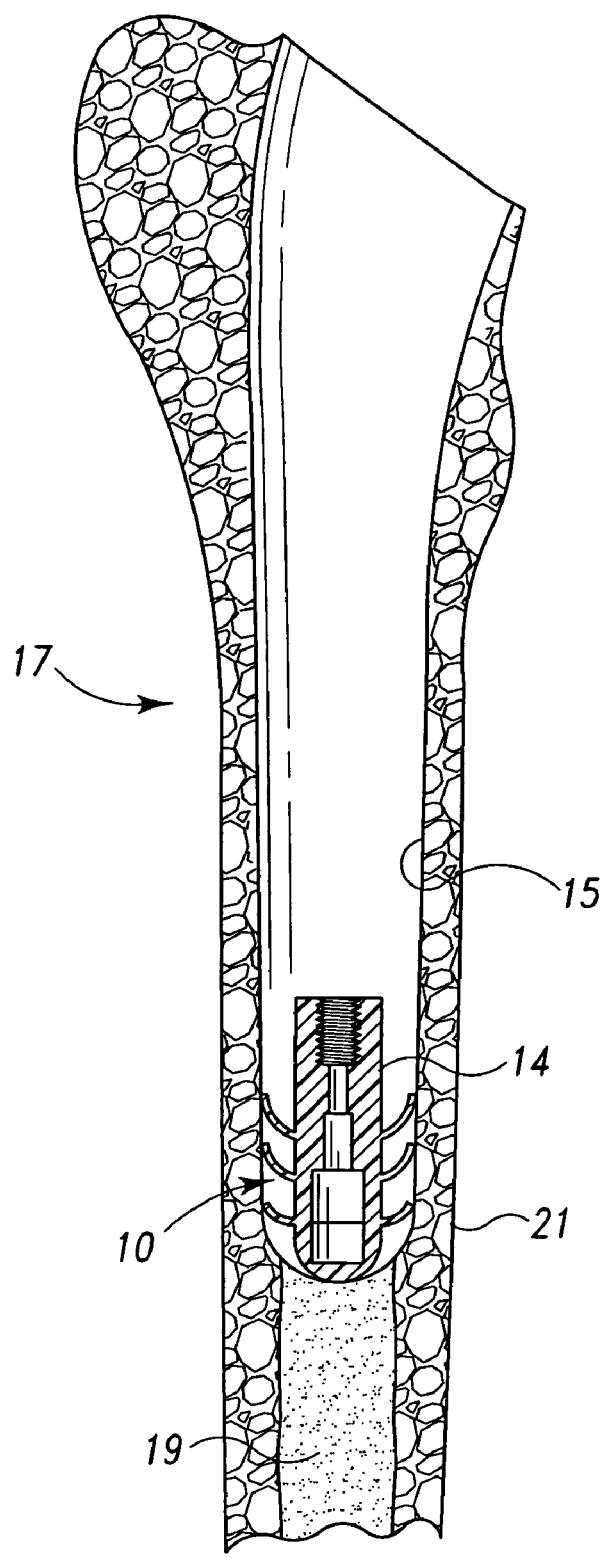
FIG. 2 is a sectional view of a resected femur showing a canal drilled in the femur and the cement restrictor placed at a distal end of the canal to restrict or block the flow of bone cement to be injected into the canal, note in FIG. 2 that the diagrammatical representation of the internal components including the power source, transmitter, modulator, and pressure transducer of the cement restrictor are not shown for clarity of description.

An illustrative cement restrictor 10 as shown in FIG. 1 is provided to act as a distal plug for bone cement mantle in a cemented total hip replacement (THR), for example. In general, the cement restrictor 10 is placed within a canal 15 drilled in a patient's femur 17 to prevent cement injected into the canal 15 from migrating or leaking into an undrilled portion of the medullary canal 19 of the patient's femur, as shown in FIG. 2. The cement restrictor 10, therefore, acts as a plug and is inserted into the distal end 21 of the pre-drilled canal of the femur 17 using a surgical insertion tool (not shown). The cement restrictor 10 of the present disclosure includes a pressure transducer 12 to monitor the pressure of the bone cement injected into the femoral canal 15, as is discussed in greater detail below.

Illustratively, as shown in FIG. 1, the cement restrictor 10 includes a body 14 and radial fins 16 extending outwardly from the body 14 which allow the cement restrictor 10 to be placed within femoral canals of various sizes; however, other cement restrictors which do not include radial fins may be used as well. Further, various body sizes for the restrictor 10 may be used for placement of the restrictor within canals of various sizes. The body 14 and the radial fins 16 are implantable and biocompatible and may illustratively be resorbable and/or include high density polyethylene (HDPE). The body 14 of the cement restrictor includes a threaded bore 18 formed to receive a corresponding threaded portion of a surgical insertion tool (not shown). Although a threaded connection between the cement restrictor 10 and the insertion tool is shown, other suitable connections may be used as well.

The pressure transducer 12 of the cement restrictor 10 is positioned within a first central cavity 20 of the body 14 of the restrictor 10. Illustratively, a passageway or channel 22 of the body 14 extends between the first central cavity 20 containing the pressure transducer 12 and the threaded bore 18. Illustratively, the threaded bore 18 is formed through an outer surface 24 of the body 14 and is, therefore, in communication with the surrounding environment. As such, the pressure transducer 12 is also in communication with the surrounding environment via the channel 22. Although various pressure transducers may be used, one such pressure transducer is the Ultra-Miniature Single Pressure Sensor Intravascular Mikro-Tip Pressure Catheter made by Millar® Instruments (Houston, Tex.), for example. As is discussed in further detail below, the pressure transducer 12 monitors the pressure of the bone cement as the bone cement is injected into the femoral canal.

The cement restrictor 10 further includes an internal power generator or power source 26 positioned within a second central cavity 28 of the body 14. The power source 26 is electrically coupled to the pressure transducer 12 to power the pressure transducer 12. A transmitter 30 of the cement restrictor 10 is electrically coupled to the pressure transducer 12 to receive an output pressure signal of the pressure transducer 12. The transmitter 30 is positioned within a third central cavity 32 of the body 14 of the restrictor 10. The power source 26 is electrically coupled to the transmitter 30 to power the transmitter 30 to transmit the output pressure signal of the pressure transducer 12 to a remote receiver 34.

As shown in the partially schematic view of FIG. 1, the cement restrictor 10 is part of a distal pressure measurement system 11. The distal pressure measurement system 11 includes both the cement restrictor 10, which is implanted into a patient, and an external component system 13 in communication with the cement restrictor 10. Illustratively, the external component system 13 includes the remote receiver 34 to receive the output signal of the pressure transducer 12 sent by the internal transmitter 30. As is discussed below, the external system 13 may include other components as well.

The internal power source 26 of the cement restrictor 10 may take many forms. For example, the power source 26 may be an on-board battery, such as a lithium iodine cell available from Wilson Greatbatch Technologies, Inc. (Clarence, N.Y.). As mentioned above, the battery would then be connected to both the pressure transducer 12 and the transmitter 30 so that each of these components has a continuous supply of power to continuously monitor and transmit the pressure of the bone cement.

Alternatively, the internal power source 26 of the cement restrictor 10 may be an inductive power source such as a ferrite coil. A suitable ferrite coil is a small wound coil such as that available commercially from MicroStrain, Inc. (Williston, Vt.), for example. The necessary characteristics of such a wound coil may depend to some extent on the design and selection of the other electronic components; power, frequency, and size of the coil can be adjusted to suit the other components of the system. Alternatively, a suitable ferrite coil may be wound using standard equipment such as that available from Aumann North America, Inc. (Fort Wayne, Ind.). When the coil is passed through an externally generated electromagnetic or magnetostatic field an electric current is formed through the coil which may be used to power the other components within the cement restrictor 10. The power source 26 may also be a radio frequency transducer configured to produce an electric current in response to radio waves. Other suitable power sources or power generators may be used as well.

Illustratively, the transmitter 30 is a radio-frequency (RF) transmitter and the receiver 34 is an RF receiver. Suitable RF transmitters are commercially available from Texas Instruments, Inc. in the form of electronic chips. The desired characteristics of the transmitter may vary depending on other components of the system; in general, the transmitter 30 may be configured to be of an appropriate size for fitting within the body of a typical cement restrictor, to transmit at a desired frequency, and to not consume excessive power. Moreover, it should be understood that the present invention is not limited to any particular type of transmitter or transmission signal unless expressly called for in the claims.

Although an RF transmitter is described above, other suitable transmitters 30 may be used as well to transmit the output pressure signal from within the patient's body to a remote receiver located outside the patient's body. Other possible types of transmitters and types of signals include optical data transmission. An IBM personal area network may also be a suitable transmitter. Acoustic energy transmission, capacitive telemetry (using electric fields) and inductive telemetry (using magnetic fields) are also possible alternatives for transmission in the present invention. Illustratively, the transmitter 30 may include an internal antenna and/or may be electrically connected or coupled to an internal antenna (not shown). A suitable antenna is available from Microstrain (Willison, Vt.).

For embodiments where the power source 26 includes an inductor, an external power source 44 may be provided (as shown in FIG. 1) at the point of care. The external power source 44 forms a portion of the external component system 13 and may include an external coil that generates a strong localized electromagnetic or magnetostatic field that acts upon the implanted ferrite coil to thereby supply power to the implanted electronics. Suitable external coils are commercially available from Microstrain Inc. (Williston, Vt.). Generally, since the external coils 44 are likely to be used in close proximity to the patient, it may be desirable to select or design an external coil that will not irritate or excessively heat the patient's skin and that can be easily handled by the operator or medical technician. The external coil 44 should be able to supply a sufficient field at the design frequency to stimulate the internal power coil.

As shown in FIG. 1, the external receiver 34 and a data interpretation and/or display device 46 may also be provided at the point of care, such as within the OR of the hospital where the THR procedure is being conducted, for example. The external receiver 34 may include a RF antenna that is connected to receive the signal from the internal antenna of the RF transmitter 30 and to provide a signal to the data interpretation device 46. The data interpretation device 46 may be a standard computer programmed to demodulate the RF signal received from the receiver 34 and display the signal to the surgeon or other technicians and is discussed in greater detail below.

As shown in FIG. 1, the cement restrictor 10 may also include a modulator 40 to convert the output pressure signal of the pressure transducer 12 to an encoded signal that can be transmitted from the internal transmitter 30 to a location outside the patient's body. For example, the modulator 40 can encode a particular pressure output signal into an RF wave by means of varying signal amplitude, frequency, or phase. The modulator 40 is electrically connected or coupled to the transmitter 30 so that this RF wave can be transmitted outside of the patient's body through an internal antenna of the transmitter 30. Illustratively, the modulator 40 is positioned within cavity 32. Suitable modulators are commercially available from Texas Instruments, Inc. (Dallas, Tex.) in the form of electronic chips. Although the modulator and transmitter are illustrated as separate elements, a single element may be used to perform both of these functions. In other words, it is also within the scope of this disclosure for the transmitter 30 itself to include a modulator or a modulating component. The modulator is also electrically coupled to and powered by the power source 26.

Looking again to FIG. 1, the external receiver 34 is coupled to the data interpretation device 46 which may be provided at the point of care, such as in the operating room, for example, where the total hip replacement or other such procedure is taking place. Illustratively, therefore, the data interpretation device 46, in addition to the external receiver 34, both form a portion of the external component system 13. The external receiver 34 may include an RF antenna that is connected to receive the signal from the internal antenna of the cement restrictor 10 and to provide a second signal to the data interpretation device 46. The data interpretation device may be a standard computer programmed to demodulate the RF signal received from the internal transmitter 30 and internal antenna. The data interpretation device 46 may also be a hand-held personal computer, a personal desk assistant, a laptop computer or any custom-designed data acquisition device. The data interpretation device 46 may be programmed to perform calculations necessary to convert the received and demodulated signal to the pressure seen by the pressure transducer 12.

As mentioned above, the pressure transducer 12 is powered by the internal power generator or power source 26 which may include a self-contained battery or a ferrite coil acted upon by a magnetic field produced, if needed, by the external power source 44. The pressure transducer 12 monitors the pressure of the cement being injected into the femoral canal and converts this to an output pressure signal. The modulator 40 converts the output pressure signal received from the pressure transducer 12 into a transmittable signal and the transmitter 30 transmits the transmittable output pressure signal in the form of a modulated RF wave, for example, through an internal antenna. An external antenna of the receiver 34 receives the transmitted output pressure signal that has been encoded by the modulator 40 and this encoded signal is interpreted in the external computer 46 to provide the pressure in the form of a numerical value for use by the caregiver.

In use, a surgeon or other technician begins the THR by preparing the patient's femur for receiving the hip implant. For example, as shown in FIG. 2, the femur 17 is resected and a bore or canal 15 is drilled into the femur. Once the canal 15 has been drilled and/or cleaned, the cement restrictor 10 is inserted into the distal end 21 of the canal 15 to operate as a plug to prevent pressurized cement (not shown) injected at a later time from migrating into the undrilled portions of patient's femoral medullary canal 19. Further, the cement restrictor 10 of the present disclosure operates to monitor the pressure of the bone cement as it is being injected into the canal 15 to provide feedback to the surgeon or other technician as to the bone cement pressure at a distal end of the patient's bone.

Once the cement restrictor 10 has been properly placed at the distal end 21 of the canal 15, the canal 15 may be further prepared by brushing, cleaning, ravaging and/or drying. If an onboard battery is not being used to as the power source, the cement restrictor 10 may be energized by placing the portion of the patient's leg containing the cement restrictor 10 into a localized magnetic field, as discussed above. Once the power has been provided to the cement restrictor 10, pressurized cement is then injected into the canal 15 and around the cement restrictor 10. As the pressurized cement is injected into the pre-drilled canal, the pressurized cement enters the threaded bore 18 of the restrictor 10 and travels through the passageway 22 formed in the body 14 of the restrictor 10 to engage and act upon the pressure transducer 12. As such, the pressure transducer 12 senses the pressure of the cement at the distal end 21 of the femoral canal 15 to produce the output pressure signal. Once the cement has been injected into the canal 15 and pressurized within the canal 15, the implant or hip stem is slid into the cement-filled canal and properly positioned within the canal 15. The bone cement is then allowed to set. The cement restrictor 10 of the present disclosure may be used with Other implants or methods of The output pressure signal produced by the pressure transducer 12 is modulated by the modulator 40 for transmission via the transmitter 30 to the external receiver 34 to be demodulated and displayed by the data interpretation device 46 for the surgeon or other technician to read. As such, the surgeon or other technician is provided with real-time feedback as to the pressure of the cement at the distal end of the femoral canal and can adjust the pressure of the cement being injected into the canal accordingly. For example, the surgeon may inject pressurized cement at a first pressure into the pre-drilled bone canal and monitor the pressure of the bone cement at the distal end of the bone canal 15 via a wireless communication originating from the distal end 21 of the bone canal 15. Illustratively, the wireless communication is the modulated output signal from the pressure transducer 12 sent by the transmitter 30 to the external receiver 34.

The surgeon may then adjust the pressure of the pressurized cement from the first pressure to a second pressure in response to the monitored pressure of the pressurized cement at the distal end 21 of the bone canal to then inject the pressurized cement at the second pressure into the bone canal. Illustratively, once the bone cement polymerizes and sets, the cement restrictor 10 may be left in place to remain at the distal end 21 of the pre-drilled canal 15. It is within the scope of this disclosure to use the distally-placed cement restrictor 10 alone or in conjunction with a proximal pressure-sensing device to provide the surgeon or other technician with a complete picture of the pressure profile of the bone cement within the femoral canal.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A device for implantation into a bone comprising:
a cement restrictor comprising:
a body including a plurality of radial fins extending outwardly therefrom, the body sized to prevent cement injected into a canal in the bone from migrating beyond the distal end of the canal,
a pressure transducer operable to measure the pressure of cement at the distal end of the canal, and
a transmitter electrically coupled to the pressure transducer and configured to transmit an output signal of the pressure transducer,
wherein the pressure transducer and transmitter are secured to the body.

2. The device of claim 1, wherein the transmitter is a radio frequency transmitter.

3. The device of claim 1, wherein the transmitter is an acoustic energy transmitter.

4. The device of claim 1, further including a power source secured to the body and electrically coupled to the pressure transducer and the transmitter.

5. The device of claim 4, wherein the power source is a battery.

6. The device of claim 4, wherein the power source is a ferrite coil configured to produce an electric current when subjected to a magnetic field.

7. The device cement restrictor of claim 1, wherein
the body includes a channel in communication with the surrounding environment, and
the pressure transducer is positioned such that the pressure transducer is also in communication with the surrounding environment via the channel of the body.

8. The device of claim 7, wherein the body is resorbable.

9. The device of claim 7, wherein the body includes high density polyethylene.

10. The device of claim 7, wherein the body includes a threaded bore in communication with the channel and is configured to receive a mating portion of a surgical insertion tool.

11. The device of claim 1, wherein the transmitter includes
a modulator configured to modulate the output pressure signal into a radio wave, and
an antenna configured to transmit the modulated output pressure signal to a remote receiver.

12. A bone cement measurement system for measuring the pressure of the bone cement within a distal portion of a pre-drilled canal of a patient's bone, the bone cement measurement system comprising:
a cement restrictor having a body, the body including a plurality of radial fins extending outwardly therefrom, a power source, a pressure transducer electrically coupled to the power source, and a transmitter electrically coupled to the power source to transmit an output signal of the pressure transducer, and
an external receiver to receive the output signal sent from the transmitter.

13. The bone cement measurement system of claim 12, further comprising a display device coupled to the external receiver to display the output signal.

14. The bone cement measurement system of claim 12, wherein the power source is an internal coil and further including an external coil to produce a magnetic field to power the internal coil.

15. A method of measuring the pressure within a distal end of a bone canal during cement pressurization of the canal, the method comprising the steps of:
inserting a body including a plurality of radial fins extending outwardly therefrom and a pressure transducer into the distal end of the bone canal, the body being sized to prevent cement injected into a canal in the bone from migrating beyond the distal end of the canal,
inserting pressurized bone cement into the bone canal,
reading an output signal from the pressure transducer, and
adjusting the pressure of the pressurized bone cement being injected into the bone canal in response to the output signal.

16. The method of claim 15, wherein the step of reading an output signal from the pressure transducer includes transmitting the output signal of the pressure transducer to a remote receiver.

17. A method of injecting pressurized cement into a pre-drilled bone canal, the method comprises the steps of:
injecting pressurized cement at a first pressure into the pre-drilled bone canal, monitoring the pressure of the pressurized cement at a distal end of the bone canal via a wireless communication originating from a body including a plurality of radial fins extending outwardly therefrom that is positioned within the distal end of the bone canal, adjusting the pressure of the pressurized cement from the first pressure to a second pressure in response to the monitored pressure of the pressurized cement at the distal end of the bone canal, and injecting pressurized cement at the second pressure into the pre-drilled bone canal.

18. The method of claim 17, wherein monitoring the pressure of the pressurized cement at the distal end of the bone canal includes reading the pressure at the distal end of the bone canal using an implanted pressure transducer coupled to the body within the distal end of the bone canal and transmitting an output signal of the pressure transducer to a remote receiver.

19. The method of claim 18, wherein transmitting the output signal of the pressure transducer to a remote receiver includes modulating the output signal to a radio frequency wavelength.

* * * * *